(12) United States Patent
Kim et al.

(10) Patent No.: US 11,594,332 B2
(45) Date of Patent: Feb. 28, 2023

(54) DEVICE, METHOD, AND COMPUTER PROGRAM FOR SELF-DIAGNOSIS AND TREATMENT OF BENIGN PAROXYSMAL POSITIONAL VERTIGO

(71) Applicant: DZMED, INC., San Jose, CA (US)

(72) Inventors: Ji-Soo Kim, Seongnam-Si (KR); Hyo-Jung Kim, Seongnam-Si (KR)

(73) Assignee: DZMED, INC., San Jose, CA (US)

( * ) Notice: Subject to any disclaimer, the term of this patent is extended or adjusted under 35 U.S.C. 154(b) by 682 days.

(21) Appl. No.: 16/663,973

(22) Filed: Oct. 25, 2019

(65) Prior Publication Data

US 2020/0126665 A1 Apr. 23, 2020

Related U.S. Application Data

(63) Continuation-in-part of application No. PCT/KR2018/004903, filed on Apr. 27, 2018.

(30) Foreign Application Priority Data

Apr. 28, 2017 (KR) .................... 10-2017-0055316

(51) Int. Cl.
*G16H 50/20* (2018.01)
*G16H 30/20* (2018.01)
(Continued)

(52) U.S. Cl.
CPC ............ *G16H 50/20* (2018.01); *G16H 10/20* (2018.01); *G16H 30/20* (2018.01); *G16H 70/20* (2018.01)

(58) Field of Classification Search
None
See application file for complete search history.

(56) References Cited

U.S. PATENT DOCUMENTS 6,609,523 B1 8/2003 Anthony
6,918,769 B2 * 7/2005 Rink ...................... G09B 5/065
434/362

(Continued)

FOREIGN PATENT DOCUMENTS

JP 2001-273362 A 10/2001
KR 10-2004-0108098 A 12/2004
(Continued)

OTHER PUBLICATIONS

Gold, Daniel R., et al. "Repositioning maneuvers for benign paroxysmal positional vertigo." Current treatment options in neurology 16.8 (2014): 1-22.*

(Continued)

*Primary Examiner* — Sultana M Zalalee
(74) *Attorney, Agent, or Firm* — Fenwick & West LLP

(57) ABSTRACT

Provided are a device, a method, and a computer program for self-diagnosis and treatment of benign paroxysmal positional vertigo, which is for, when a patient with benign paroxysmal positional vertigo develops or appeals symptoms, immediately, easily and accurately diagnosing the symptoms by patients themselves using a sequential and efficient self-diagnosis algorithm associated with an optimized self-diagnosis questionnaire data without temporal or spatial constraints, and presenting an optimal treatment method, so as to allow the patients to receive appropriate on-site treatments. The present disclosure is effective in not only immediate treatment of benign paroxysmal positional vertigo, but also reducing medical expenses and additional social costs incurred for treatments of dizziness.

16 Claims, 8 Drawing Sheets

(51) Int. Cl.
G16H 10/20 (2018.01)
G16H 70/20 (2018.01)

(56) References Cited

U.S. PATENT DOCUMENTS

| | | | | |
|---|---|---|---|---|
| 2008/0162393 A1* | 7/2008 | Iliff | ........................ | G16H 40/67 |
| | | | | 706/46 |
| 2008/0183504 A1* | 7/2008 | Highley | ................. | G06Q 30/04 |
| | | | | 705/34 |
| 2009/0281392 A1* | 11/2009 | Brown | ................. | A61B 5/0002 |
| | | | | 600/300 |
| 2011/0064204 A1* | 3/2011 | Clawson | ................ | G16H 50/30 |
| | | | | 379/45 |
| 2011/0112855 A1* | 5/2011 | Chen | ....................... | G16H 70/20 |
| | | | | 705/2 |
| 2013/0040271 A1* | 2/2013 | Rytky | ..................... | G16H 20/30 |
| | | | | 434/247 |
| 2018/0049663 A1 | 2/2018 | Suh et al. | | |

FOREIGN PATENT DOCUMENTS

| | | | |
|---|---|---|---|
| KR | 10-2010-0013821 | A | 2/2010 |
| KR | 10-2014-0120615 | A | 10/2014 |
| KR | 10-2014-0128630 | A | 11/2014 |
| KR | 10-2015-0144851 | A | 12/2015 |
| WO | 2018-199678 | A | 11/2018 |

OTHER PUBLICATIONS

Eun-Ju Jeon et al., "Multicenter Study on the Clinician's Diagnostic and Therapeutic Approaches for Benign Paroxysmal Positional Vertigo in Korea," Research in Vestibular Science, 2013, vol. 12, No. 3, pp. 79-92.
Seung-Han Lee, "Diagnostic criteria of BPPV," The 34th Conference of the Korean Neurological Association, 2015, pp. 257-260.
Ji-Soo Kim et al., "Benign Paroxysmal Positional Vertigo," The new England Journal of Medicine, 2014, vol. 370, pp. 1138-1147.
C. R. Gordon et al., "Repeated vs single physical maneuver in benign paroxysmal positional vertigo," Acta Neural Scand, 2004, vol. 110, pp. 166-169.
A. Radtke et al., "Self-treatment of benign paroxysmal positional vertigo: Semont maneuver vs Epley procedure," Neurology, 2004, vol. 63, pp. 150-152.
Joseph M. Furman et al., "Do try this at home: self-treatment of BPPV," Neurology, 2004, vol. 63, pp. 8-9.
Hitoshi Tanimoto et al., "Self-treatment for benign paroxysmal positional vertigo of the posterior semicircular canal," Neurology, 2005, vol. 65, pp. 1299-1300.
Robert A. Nunez et al., "Short- and long-term outcomes of canalith repositioning for benign paroxysmal positional vertigo," Otolaryngology—Head and Neck Surgery, 2000, vol. 122, pp. 647-652.
M. Sakaida et al., "Long-term outcome of benign paroxysmal positional vertigo," Neurology, 2003, vol. 60, pp. 1532-1534.
Hyo-Jung Kim et al., "The Patterns of recurrences in idiopathic Benign Paroxysmal Positional Vertigo and Self-treatment Evaluation," Frontiers in Neurology, 2017, vol. 8, Article 690.
Kayoko Higachi-Shingai et al., "Diagnosis of the subtype and affected ear of benign paroxysmal positional vertigo using a questionnaire," Acta Oto-Laryngologica, 2011, vol. 131, pp. 1264-1269.
Li Lin et al., "Formulation and evaluation of diagnostic questionnaire for benign paroxysmal positional vertigo," National Medical Journal of China, 2017, vol. 97, No. 14, pp. 1061-1064.
Joseph A. McClure et al., "Horizontal canal BPV," The Journal of otolaryngology 1985, vol. 14, pp. 30-35.
Robert W. Baloh et al., "Horizontal semicircular canal variant of benign positional vertigo," Neurology, 1993, vol. 43, pp. 2542-2549.
M. R. Dix et al., "The Pathology, Symptomatology and Diagnosis of Certain Common Disorders of the Vestibular System," Proceedings of the Royal Society of Medicine, 1952, vol. 45, pp. 341-354.
Michael von Breverna et al., "Benign paroxysmal positional vertigo: Diagnostic criteria," Journal of Vestibular Research, 2015, vol. 25, pp. 105-117.
Jacob Cohen, "A Coefficient of agreement for nominal scales," Educational and Psychological Measurement, 1960, vol. 20, No. I, pp. 37-46.
Thomas Brandt et al., "Benign paroxysmal positioning vertigo: A long-term follow-up (6-17 years) of 125 patients," Acta Oto-Laryngologica, 2006, vol. 126, pp. 160-163.
Jose A. Lopez-Escamez et al., "Impact of Treatment on Health-Related Quality of Life in Patients with Posterior Canal Benign Paroxysmal Positional Vertigo," Otology & Neurotology, 2003, vol. 24, pp. 637-641.
Marianne Dieterich et al., "Functional dizziness: from phobic postural vertigo and chronic subjective dizziness to persistent postural-perceptual dizziness," Current Opinion in Neurology, 2017, vol. 30, pp. 107-113.
Ellen Lindell et al., "Asking about dizziness when turning in bed predicts examination findings for benign paroxysmal positional vertigo," Journal of Vestibular Research, 2018, vol. 28, pp. 339-347.
Burak Omur Cakir et al., "What Is the True Incidence of Horizontal Semicircular Canal Benign Paroxysmal Positional Vertigo?," Otolaryngology—Head and Neck Surgery, 2006, vol. 134, pp. 451-454.
Evangelos Anagnostou et al., "Diagnosis and Treatment of Anterior-Canal Benign Paroxysmal Positional Vertigo: A Systematic Review," Journal of Clinical Neurology, 2015, vol. 11, pp. 262-267.
Corinna Lechner et al., "Causes and characteristics of horizontal positional nystagmus," Journal ofNeurol, 2014, vol. 261, pp. 1009-1017.
PUBMED English Abstract of Cui X et al, "The analysis of nystagmus in patients with posterior canal benign paroxysmal positional vertigoin positioning test," Lin Chung Er Bi Yan Hou Tou Jing Wai Ke Za Zhi., 2015, vol. 29, No. 1, pp. 27-30.
Aug. 14, 2018—International Search Report—PCT/KR2018/004903.
Written Opinion, Korean Intellectual Property Office Patent Application No. 1020170055316, dated Dec. 18, 2018, 12 pages.
Written Opinion, Patent Cooperation Treaty Application No. PCT/KR2018/004903, dated Aug. 14, 2018, 13 pages.

* cited by examiner

| | |
|---|---|
| Question 1 | Did you feel dizzy as if you or your surroundings are spinning? |
| Question 2 | Do you feel dizzy upon head movements from sitting still or lying position? |
| Question 3 | How long does the dizziness caused by head movements last? Does it last for three minutes or more, or less than three minutes? |
| Question 4 | When lying down or getting up, and when turning head to the left or right side while lying down, which is the posture that usually evokes more severe dizziness? |
| Question 5 | Does spinning dizziness disappear upon turning the head to the left or right side while lying down within one minute? Or does it last for one minute or more? |
| Question 6 | When lying down with the head on the right side and when lying down with the head on the left side, on which side is the dizziness more severe? |

FIG. 6

| Non-BPPV | Left Apogeotropic HC-BPPV | Right Apogeotropic HC-BPPV | Left Geotropic HC-BPPV | Right Geotropic HC-BPPV | Left PC-BPPV / Right AC-BPPV | Right PC-BPPV / Left AC-BPPV |
|---|---|---|---|---|---|---|
| Brandt-Daroff exercise | Gufoni maneuver for left cupulolithiasis | Gufoni maneuver for right cupulolithiasis | Barbecue maneuver for Left geotropic HC_BPPV | Barbecue maneuver for Right geotropic HC_BPPV | Epley maneuver for Left HC_BPPV | Epley maneuver for Right HC_BPPV |
| 301 | 302 | 303 | 304 | 305 | 306 | 307 |

DEVICE, METHOD, AND COMPUTER PROGRAM FOR SELF-DIAGNOSIS AND TREATMENT OF BENIGN PAROXYSMAL POSITIONAL VERTIGO

CROSS-REFERENCE TO RELATED APPLICATION

This application claims priority to and is a continuation-in-part application of International Patent Application No. PCT/KR2018/004903, filed on Apr. 27, 2018, which claims priority to Korean Patent Application No. 10-2017-0055316, filed on Apr. 28, 2017. The contents of these are incorporated herein by reference in their entirety.

BACKGROUND

1. Field

The present disclosure relates to a device, a method and a computer program for self-diagnosis and treatment, and more particularly, a device, a method and a computer program for self-diagnosis and treatment of benign paroxysmal positional vertigo (BPPV), which is for, when a BPPV patient develops symptoms, immediately and accurately diagnosing the symptoms without a temporal or spatial constraint, and presenting an optimal treatment method, so as to allow the patient to receive appropriate treatments.

2. Description of the Related Art

Benign paroxysmal positional vertigo (BPPV) is a disorder of a sudden severe spinning sensation of dizziness upon changes in the position of the head, such as, for example, when lying down or getting up, or turning in bed.

In BPPV, a severe spinning sensation of dizziness disappears within three minutes when sitting still or lying down without changes in the position of the head, but dizziness recurs upon head movements.

According to national and international studies, BPPV is the most common cause of vertigo, comprising 20% of all patients with vertigo.

BPPV is a disorder in which about 80% of patients have immediate improvements in symptoms with simple repositioning treatments. Thus, its diagnosis is clear and its treatment method is simple, but high recurrence rate is the greatest reason why many patients with BPPV feel inconvenient and anxious.

BPPV is the most common cause of recurrent dizziness, and recurs in about 50% of patients, and about 15% of patients with BPPV experience recurrences within one year.

Patients are anxious that they might experience severe dizziness again and afraid that they might not receive an immediate treatment when symptoms appear again, which reduces quality of life of the patients as compared to normal people, and the consequential social and economical burden is quite serious.

Particularly, diagnosis and treatment of BPPV require a medical device to detect patients' nystagmus and a medical faculty to perform positional and repositioning maneuvers using the above device. Thus, for diagnosis and treatments of BPPV, patients themselves need to visit hospitals having appropriate medical equipments and faculty, which makes immediate diagnosis and prescription of BPPV difficult.

Even though attempts have been made to provide services for self-diagnosis or treatments of some diseases using webpage etc., accurate diagnosis and treatments of BPPV has still required medical staffs and devices.

Accordingly, in the current medical systems, patients themselves are required to visit hospitals with the medical faculty and medical equipment for diagnosis and treatment in spite of their uneasy condition due to severe dizziness from BPPV, and thus immediate and accurate diagnosis and treatment remain difficult unless the patients visit hospitals themselves, and a considerable amount of costs may be repeatedly incurred for diagnosis and treatments due to the high recurrence rate.

SUMMARY

To solve these problems, the present disclosure is directed to providing a device, a method and a computer program for self-diagnosis and treatment of benign paroxysmal positional vertigo (BPPV), which is for, when a BPPV patient develops symptoms, immediate and accurate diagnosis and treatments without temporal or spatial constraints using a service provided through a webpage without visiting a hospital in person, and further, presenting an optimal treatment method based on the diagnosis result, so as to allow the patient to receive an appropriate treatment.

Other particular objects of the present disclosure will be obviously appreciated and understood by experts or researchers in the technical field through the detailed description provided below.

To achieve the above-described object, example embodiments of the present disclosure are directed to a device for self-diagnosis and/or treatment of benign paroxysmal positional vertigo (BPPV) according to a feature of the present disclosure includes: a data transmitting unit configured to generate multi-step self-diagnosis questionnaire data related to diagnosis of BPPV and transmit the self-diagnosis questionnaire data to a user terminal via a communication network; a data receiving unit configured to receive one or more response data to the self-diagnosis questionnaire data from the user terminal; and a control unit configured to determine a final diagnosis information based on the one or more response data and a self-diagnosis algorithm associated with the self-diagnosis questionnaire data, wherein a processor performs the self-diagnosis algorithm associated with the self-diagnosis questionnaire data where a first diagnosis for diagnosing BPPV or Non-BPPV is performed; and based on a result of the first diagnosis, further diagnosis is not progressed by determining the final diagnosis information as Non-BPPV or a second diagnosis for diagnosing a location of otolith among vertical and horizontal semicircular canals is performed; and based on a result of the second diagnosis, a third diagnosis for diagnosing Geotropic-HC-BPPV or Apogeotropic-HC-BPPV is performed; and based on the result of the second diagnosis or a result of the third diagnosis, a fourth diagnosis for diagnosing a location of otolith between ears is performed.

Additionally, example embodiments of the present disclosure are directed to a device for self-diagnosis and/or treatment of BPPV according to a feature of the present disclosure includes: a user interface unit configured to provide a user with multi-step self-diagnosis questionnaire data related to diagnosis of BPPV; a data input unit configured to receive an input of one or more response data to the self-diagnosis questionnaire data; and a control unit configured to determine a final diagnosis information based on the one or more response data and a self-diagnosis algorithm associated with the self-diagnosis questionnaire data, wherein a processor performs the self-diagnosis algorithm associated with the self-diagnosis questionnaire data where a first diagnosis for diagnosing BPPV or Non-BPPV is performed; and based on a result of the first diagnosis, further diagnosis is not progressed by determining the final diagnosis information as Non-BPPV or a second diagnosis for diagnosing a location of otolith among vertical and horizontal semicircular canals is performed; and based on a result of the second diagnosis, a third diagnosis for diagnosing Geotropic-HC-BPPV or Apogeotropic-HC-BPPV is performed; and based on the result of the second diagnosis or a result of the third diagnosis, a fourth diagnosis for diagnosing a location of otolith between ears is performed.

Additionally, example embodiments of the present disclosure are directed to a method for self-diagnosis and/or treatment of BPPV using a device for self-diagnosis and/or treatment of BPPV including a data transmitting unit, a data receiving unit and a control unit according to a feature of the present disclosure includes: transmitting, by the control unit, multiple self-diagnosis questionnaire data related to diagnosis of BPPV to a user terminal through the data transmitting unit; receiving, by the data receiving unit, one or more response data to the self-diagnosis questionnaire data from the user terminal; and determining, by the control unit, a final diagnosis information based on the one or more response data and a self-diagnosis algorithm associated with the self-diagnosis questionnaire data, wherein a processor performs the self-diagnosis algorithm associated with the self-diagnosis questionnaire data where a first diagnosis for diagnosing BPPV or Non-BPPV is performed; and based on a result of the first diagnosis, further diagnosis is not progressed by determining the final diagnosis information as Non-BPPV or a second diagnosis for diagnosing a location of otolith among vertical and horizontal semicircular canals is performed; and based on a result of the second diagnosis, a third diagnosis for diagnosing Geotropic-HC-BPPV or Apogeotropic-HC-BPPV is performed; and based on the result of the second diagnosis or a result of the third diagnosis, a fourth diagnosis for diagnosing a location of otolith between ears is performed.

Additionally, example embodiments of the present disclosure are directed to a method for self-diagnosis and/or treatment of BPPV using a device for self-diagnosis and/or treatment of BPPV including a user interface unit, a data input unit and a control unit according to a feature of the present disclosure includes: providing, by the user interface unit, a user with multi-step self-diagnosis questionnaire data related to diagnosis of BPPV; receiving, by the data input unit, an input of one or more response data to the self-diagnosis questionnaire data; and determining, by the control unit, a final diagnosis information based on the one or more response data and a self-diagnosis algorithm associated with the self-diagnosis questionnaire data, wherein a processor performs the self-diagnosis algorithm associated with the self-diagnosis questionnaire data where a first diagnosis for diagnosing BPPV or Non-BPPV is performed; and based on a result of the first diagnosis, further diagnosis is not progressed by determining the final diagnosis information as Non-BPPV or a second diagnosis for diagnosing a location of otolith among vertical and horizontal semicircular canals is performed; and based on a result of the second diagnosis, a third diagnosis for diagnosing Geotropic-HC-BPPV or Apogeotropic-HC-BPPV is performed; and based on the result of the second diagnosis or a result of the third diagnosis, a fourth diagnosis for diagnosing a location of otolith between ears is performed.

According to an example embodiment of the present disclosure, the first diagnosis is associated with a first group of questionnaires including one or more questionnaire data for diagnosing BPPV or Non-BPPV, the second diagnosis is associated with a second group of questionnaires including one or more questionnaire data for diagnosing a location of otolith among vertical and horizontal semicircular canals, the third diagnosis is associated with a third group of questionnaires including one or more questionnaire data for diagnosing Geotropic-HC-BPPV or Apogeotropic-HC-BPPV, and the fourth diagnosis is associated with a fourth group of questionnaires including one or more questionnaire data for diagnosing a location of otolith between the ears, and the self-diagnosis algorithm allows a user to make self-diagnosis without other medical device.

According to an example embodiment of the present disclosure, the first group of questionnaires includes a first questionnaire data, a second questionnaire data and a third questionnaire data, the second group of questionnaires includes a fourth questionnaire data, the third group of questionnaires includes a fifth questionnaire data, and the fourth group of questionnaires includes a sixth questionnaire data, the first questionnaire data is a questionnaire about feeling dizzy as if the user or surroundings are spinning, the second questionnaire data is a questionnaire about feeling dizzy upon head movements from sitting still or lying position, the third questionnaire data is a questionnaire about whether dizziness caused by head movements lasts for three minutes or more or for less than three minutes, the fourth questionnaire data is a questionnaire about when lying down or getting up (e.g., sitting up from a lying position, etc.), and when turning the head to the left or right side while lying down, which is the posture that usually evokes more severe dizziness, the fifth questionnaire data is a questionnaire about whether spinning dizziness upon turning the head to the left or right side while lying down lasts for less than one minute or for one minute or more, and the sixth questionnaire data is a questionnaire about when lying down with the head on the right side and when lying down with the head on the left side, on which side the dizziness is more severe.

According to an example embodiment of the present disclosure, the control unit transmits the first questionnaire data, the second questionnaire data and the third questionnaire data to the user terminal through the data transmitting unit in a sequential order, and when an answer choice signal of "No" is received as response data to the first questionnaire data and the second questionnaire data and an answer choice signal of "three minutes or more" is received as response data to the third questionnaire data from the user terminal, the control unit determines as Non-BPPV.

According to an example embodiment of the present disclosure, the control unit transmits the first questionnaire data, the second questionnaire data and the third questionnaire data to the user terminal through the data transmitting unit in a sequential order, and when an answer choice signal of "Yes" is received as response data to the first questionnaire data and the second questionnaire data, and an answer choice signal of "less than three minutes" is received as response data to the third questionnaire data from the user terminal, the control unit determines as BPPV, and when an answer choice signal of "when turning the head to the left or right side while lying down" to the fourth questionnaire data is received from the user terminal, the control unit classifies as a disease type of horizontal semicircular canal, and transmits the fifth questionnaire data to the user terminal through the data transmitting unit.

According to an example embodiment of the present disclosure, when an answer choice signal of "one minute or more" is received as response data to the fifth questionnaire data, the control unit classifies as a disease type of Apogeotropic-HC-BPPV, and transmits the sixth questionnaire data to the user terminal through the data transmitting unit, and when an answer choice signal of "right side" to the sixth questionnaire data is received from the user terminal, the control unit determines the final diagnosis information as Left Apogeotropic-HC-BPPV, and when an answer choice signal of "left side" to the sixth questionnaire data is received, the control unit determines the final diagnosis information as Right Apogeotropic-HC-BPPV; and wherein when an answer choice signal of "less than one minute" to the fifth questionnaire data is received, the control unit classifies as a disease type of Geotropic-HC-BPPV, and transmits the sixth questionnaire data to the user terminal through the data transmitting unit, and when an answer choice signal of "right" to the sixth questionnaire data is received from the user terminal, the control unit determines the final diagnosis information as Right Geotropic-HC-BPPV, and when an answer choice signal of "left side" is received, the control unit determines the final diagnosis information as Left Geotropic-HC-BPPV.

According to an example embodiment of the present disclosure, the control unit transmits the first questionnaire data, the second questionnaire data and the third questionnaire data to the user terminal through the data transmitting unit in a sequential order, and when an answer choice signal of "Yes" is received as response data to the first questionnaire data and the second questionnaire data, and an answer choice signal of "less than three minutes" is received as response data to the third questionnaire data from the user terminal, the control unit determines as BPPV, and wherein when an answer choice signal of "when lying down or getting up" to the fourth questionnaire data is received from the user terminal, the control unit classifies as a disease type of vertical semicircular canal (anterior semicircular canal, posterior semicircular canal), and transmits the sixth questionnaire data to the user terminal through the data transmitting unit, when an answer choice signal of "right side" to the sixth questionnaire data is received from the user terminal, the control unit determines the final diagnosis information as Right Posterior-Canal BPPV (PC-BPPV) or Left Anterior-Canal BPPV (AC-BPPV), and when an answer choice signal of "left side" is received in the sixth questionnaire data, the control unit determines the final diagnosis information as Left PC-BPPV or Right AC-BPPV.

According to an example embodiment of the present disclosure, the device for self-diagnosis and/or treatment of BPPV further comprises a data storage unit configured to store a self-treatment method (e.g., a self-administered treatment) selected for each disease type of BPPV and created in a form of a video, and the control unit is configured to determine the final diagnosis information based on the one or more response data, search for a self-treatment method corresponding to the determined final diagnosis information in the data storage unit, and control the data transmitting unit to transmit the searched self-treatment method to the user terminal.

According to an example embodiment of the present disclosure, in case of the Left Apogeotropic Horizontal-Canal BPPV (Apogeotropic-HC-BPPV), the control unit provides the user terminal with Gufoni maneuver for left cupulolithiasis in a form of a video, and in case of the Right Apogeotropic-HC-BPPV, the control unit provides the user terminal with Gufoni maneuver for right cupulolithiasis in a form of a video.

According to an example embodiment of the present disclosure, in case of the Left PC-BPPV or Right AC-BPPV, the control unit provides the user terminal with Epley maneuver for left PC-BPPV in a form of a video, and in case of the Right PC-BPPV or Left AC-BPPV, the control unit provides the user terminal with Epley maneuver for right PC-BPPV in a form of a video.

Additionally, example embodiments of the present disclosure are directed to a computer program according to a feature of the present disclosure is a computer program stored in a computer-readable medium to enable a computer to perform each step defined in the methods for self-diagnosis and/or treatment of BPPV using a device for self-diagnosis and/or treatment of BPPV.

The self-diagnosis algorithm associated with the self-diagnosis questionnaire data, system, device and method of the present disclosure is effective in, when a patient with benign paroxysmal positional vertigo (BPPV) develops or appeals symptoms, immediate, easy and accurate on-site diagnosis without temporal or spatial constraints and providing an optimal treatment method, so as to allow the patient to receive appropriate on-site treatments, and reducing the required medical expenses and consequential social costs.

By adopting the present disclosure, BPPV or Non-BPPV can be screened in advance and then subtype and affected ear of BPPV can be determined in such an efficient and optimized way—for example in such an efficient and optimized way not to distinguish Right PC-BPPV (or Left PC-BPPV) from Left AC-BPPV (or Right AC-BPPV) since symptoms and treatment methods for Right PC-BPPV (or Left PC-BPPV) and Left AC-BPPV (or Right AC-BPPV) are same—for all patients who appeal and present dizziness with high accuracy, consistency and efficiency, and optimal on-site treatments suitable for the on-site diagnosis result can be provided to the patients immediately without bothering to consult with medical faculty and use other medical examination devices such as video-oculography.

BRIEF DESCRIPTION OF THE DRAWINGS

The above and other aspects, features and advantages of the disclosed example embodiments will be more apparent from the following detailed description taken in conjunction with the accompanying drawings in which:

FIG. 6 is an illustration showing self-diagnosis questionnaire data according to an example of the present disclosure.

FIG. 8 is an illustration showing self-diagnosis and treatment methods selected for each disease type of BPPV according to an example of the present disclosure.

DETAILED DESCRIPTION

Example embodiments are described more fully hereinafter. The example embodiments may, however, be embodied in many different forms and should not be construed as limited to the example embodiments set forth herein. In the description, details of features and techniques may be omitted to more clearly disclose example embodiments.

The terminology used herein is for the purpose of describing particular embodiments only and is not intended to be limiting. As used herein, the singular forms "a," "an" and "the" are intended to include the plural forms as well, unless the context clearly indicates otherwise. Furthermore, the use of the terms a, an, etc. do not denote a limitation of quantity, but rather denote the presence of at least one of the referenced item.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. All methods described herein can be performed in a suitable order unless otherwise indicated herein or otherwise clearly contradicted by context. The use of any and all examples, or exemplary language (e.g., "such as"), is intended merely to better illustrate the example embodiments and does not pose a limitation on the scope of the present disclosure unless otherwise claimed. No language in the specification should be construed as indicating any non-claimed element as essential to the practice of the present disclosure as used herein.

The term "comprises" or "includes" as used herein throughout this specification, specifies presence of stated elements, but does not preclude presence or addition of one or more other elements unless the context clearly indicates otherwise.

When patients with benign paroxysmal positional vertigo (BPPV) have symptoms, the present disclosure may diagnose the symptoms immediately and accurately without temporal and spatial constraints and present optimal treatment methods to allow the patients to receive appropriate treatments.

The present disclosure allows patients to diagnose and treat dizziness on-site, i.e., at home etc. immediately and accurately without a visit to the hospitals when dizziness occurs, thereby reducing medical expenses and social costs associated with dizziness.

Patients with BPPV can do repositioning maneuvers for treatments well at home themselves or with the help of guardians.

Figure 1:
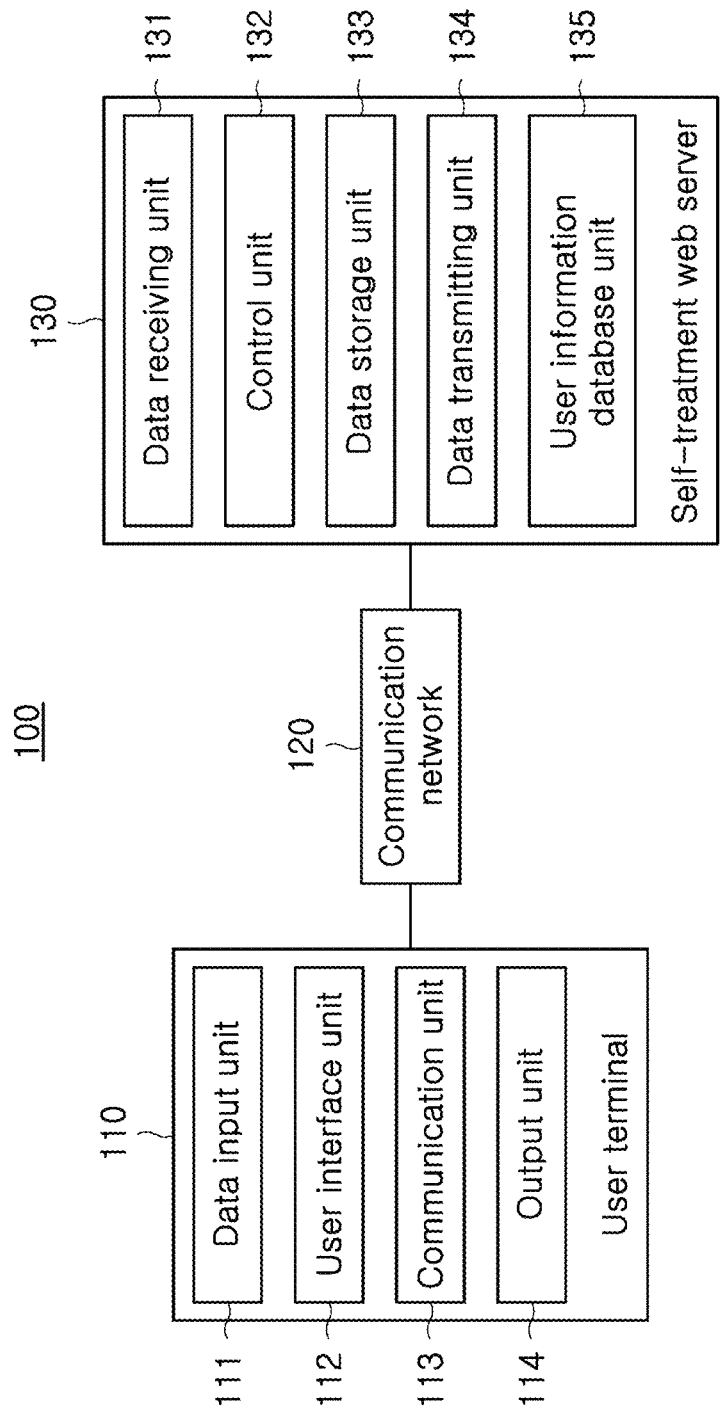
FIG. 1 is a diagram showing a configuration of a system for self-diagnosis and treatment of benign paroxysmal positional vertigo (BPPV) according to an example of the present disclosure.
Figure 2:
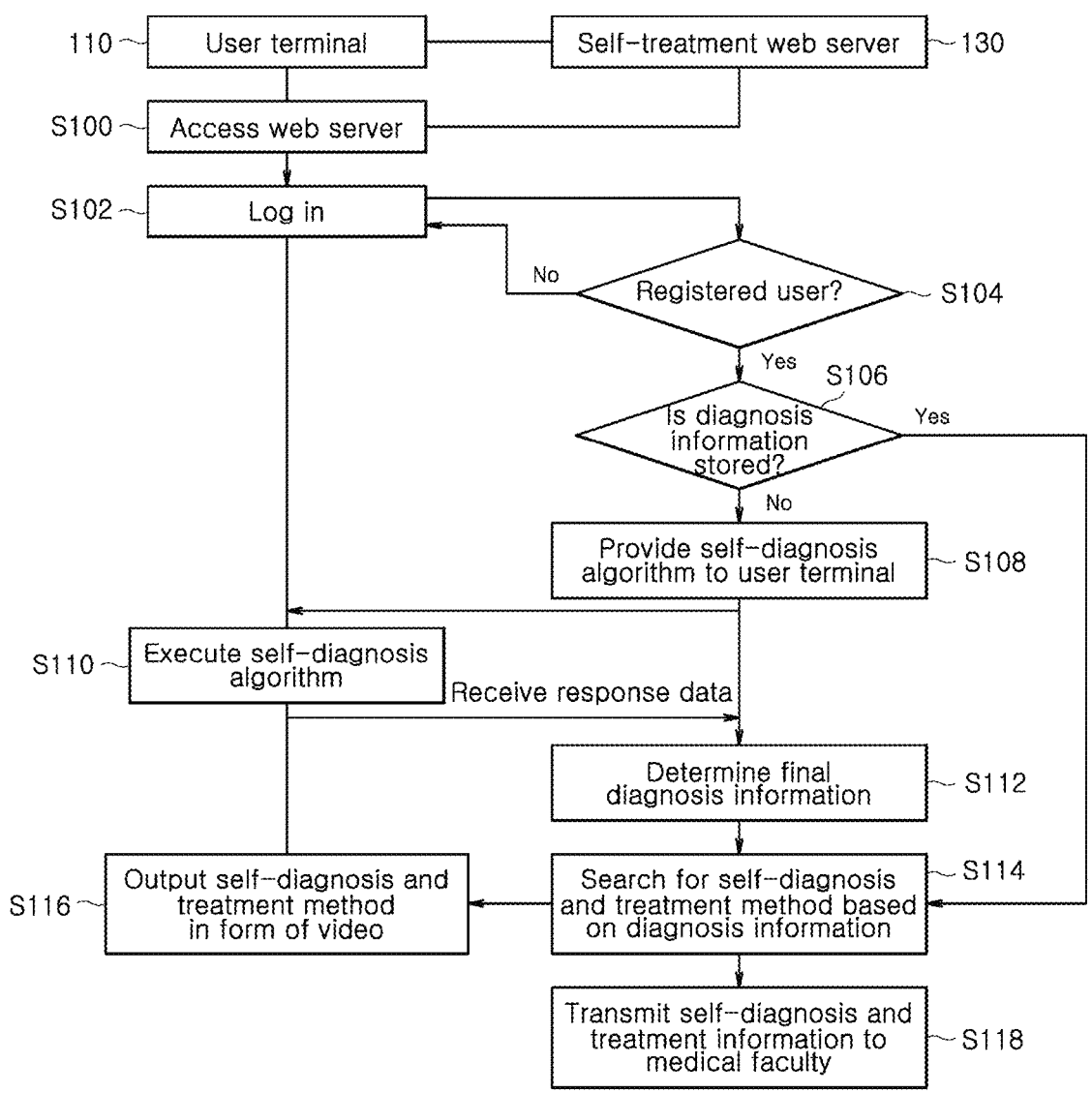
FIG. 2 is a diagram showing a method for self-diagnosis and treatment of BPPV according to an example of the present disclosure.
Figure 3:
FIG. 3 is an illustration showing an example of a self-treatment service webpage provided to a user terminal according to an example of the present disclosure.
Figure 4:
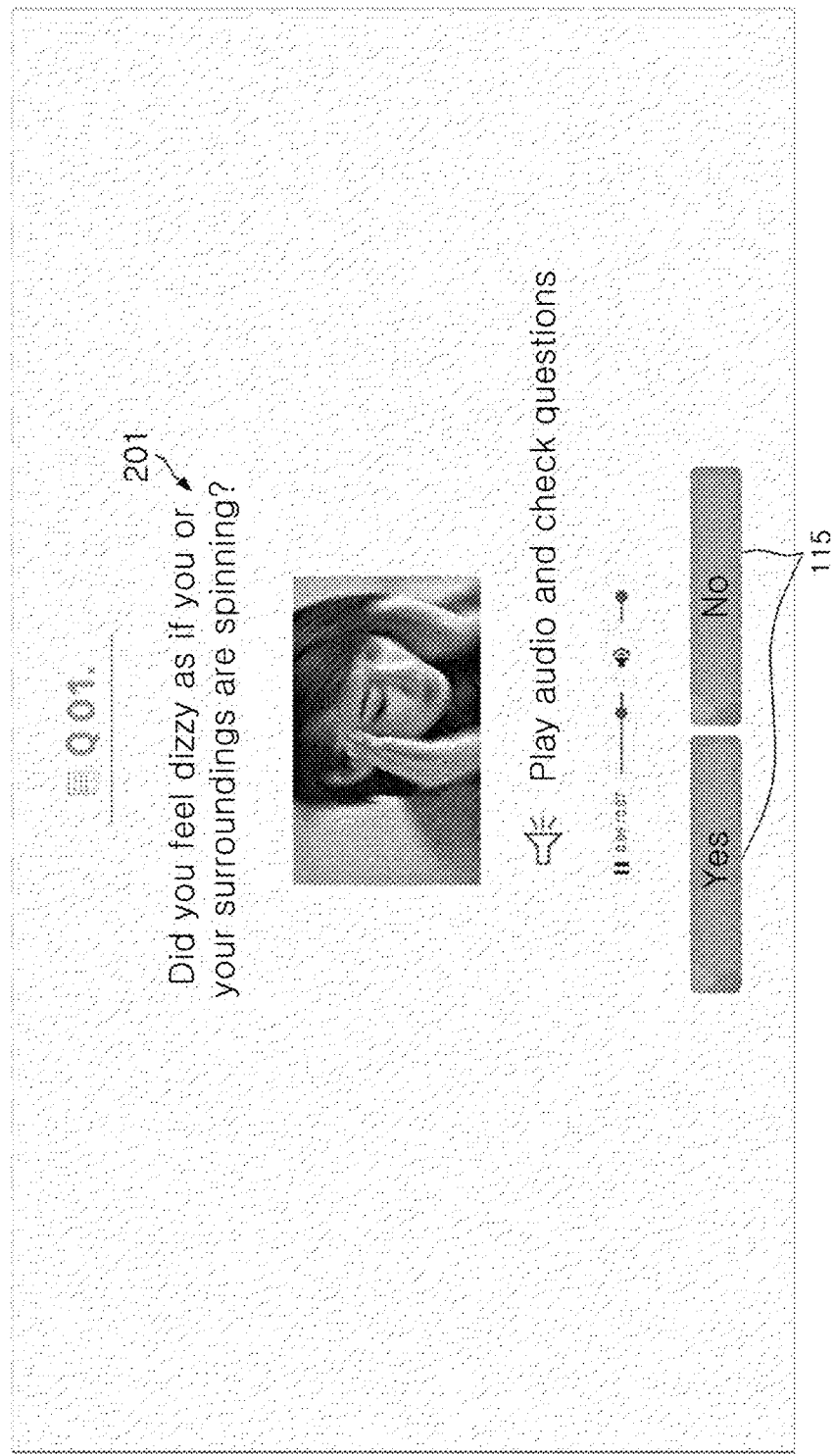
FIG. 4 is an illustration showing an example of self-diagnosis questionnaire data provided to a user terminal according to an example of the present disclosure.
Figure 5:
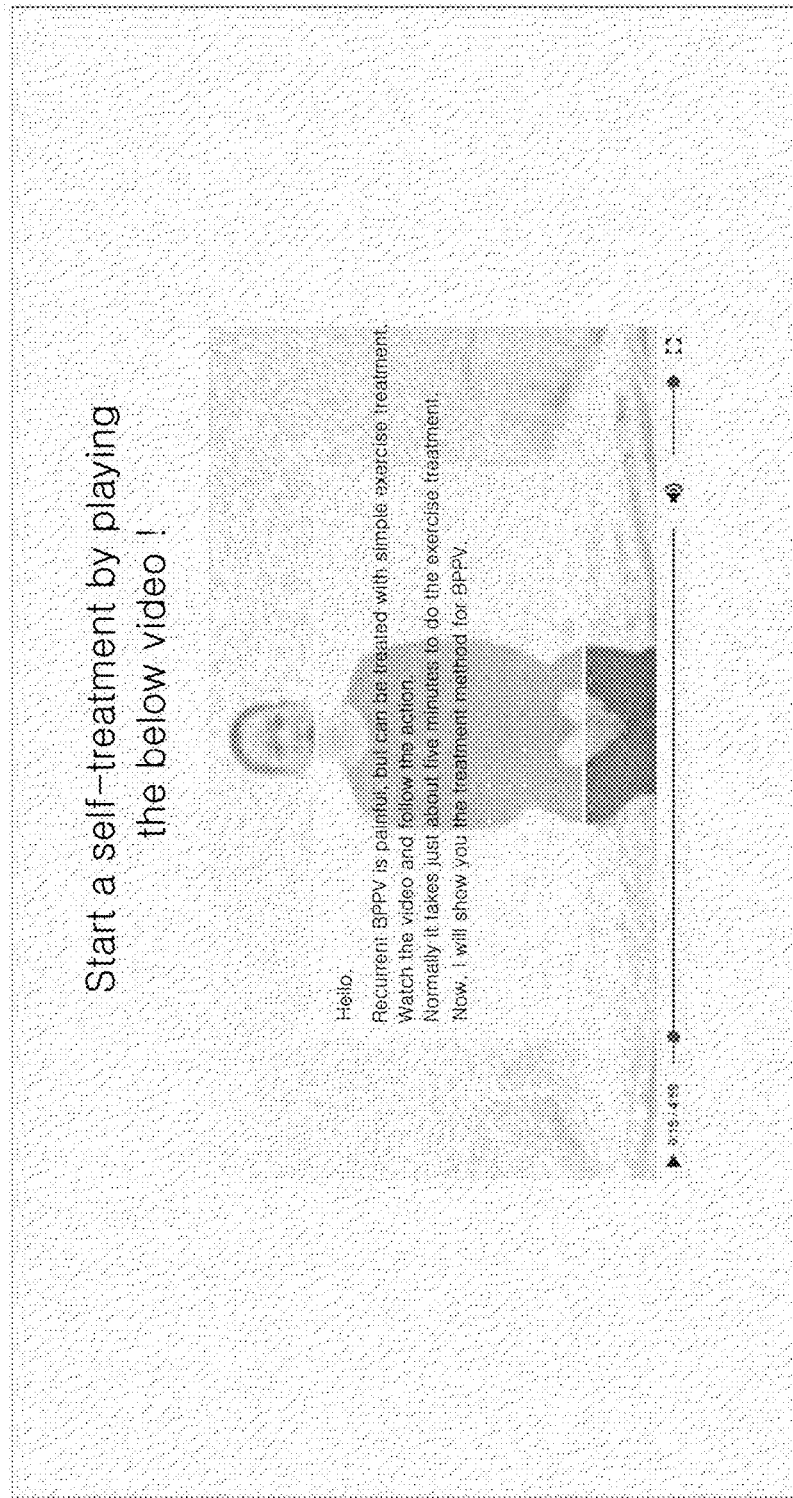
FIG. 5 is an illustration showing an example of a self-diagnosis and treatment method outputted on a user terminal according to an example of the present disclosure.

FIG. 1 is a diagram showing a configuration of a system for self-diagnosis and treatments of BPPV according to an example of the present disclosure, FIG. 2 is a diagram showing a method for self-diagnosis and treatments of BPPV according to an example of the present disclosure, FIG. 3 is an illustration showing an example of a self-treatment service webpage provided to a user terminal according to an example of the present disclosure, FIG. 4 is an illustration showing an example of self-diagnosis questionnaire data (e.g., questions) provided to a user terminal according to an example of the present disclosure, FIG. 5 is an illustration showing an example of a self-diagnosis and treatment method outputted on a user terminal according to an example of the present disclosure, and FIG. 6 is an illustration showing self-diagnosis questionnaire data according to an example of the present disclosure.

The system 100 for self-diagnosis and treatment of BPPV according to an example of the present disclosure includes a user terminal 110, a communication network 120 and a self-treatment web server 130.

As is shown in FIG. 1, the user terminal 110 may include a data input unit 111, a user interface unit 112, a communication unit 113 and an output unit 114, and the self-treatment web server 130 may include a data receiving unit 131, a control unit 132, a data storage unit 133, a data transmitting unit 134 and a user information database unit 135. The communication network 120 may be a wired communication network, for example, Internet, and may be a wireless communication network, for example, a mobile communication network.

In this instance, the user terminal 110 may include a wired terminal or a wireless terminal equipped with a web browser based on the programming language such as Hypertext Preprocessor (PHP), HTML (Hypertext Markup Language) 5 and jQuery, and may include not only a wired terminal such as a desktop PC but also a mobile device such as a smart phone, PDA and a tablet PC.

Hereinafter, although an example of the present disclosure shows that the user terminal 110 accesses the self-treatment web server 130 to perform webpage-based diagnosis and treatments of BPPV, the present disclosure is not necessarily limited thereto, and the present disclosure may be implemented using various forms including webpages etc. by accessing the web server as well as various servers through a dedicated App that runs on the user terminal 110.

Further, although the following description primarily illustrates that the user terminal 110 connects to the self-diagnosis web server 130 and the self-diagnosis web server 130 performs diagnosis of BPPV, the present disclosure is not necessarily limited thereto, and otherwise it is possible that the user terminal 110 directly performs diagnosis of BPPV.

Hereinafter, the system 100 for self-diagnosis and treatments of BPPV according to an example of the present disclosure will be described in more details with reference to the accompanying drawings.

The user terminal 110 accesses the self-treatment web server 130 using an ID and a password allocated by a user who intends to treat BPPV (S100). BPPV may be also known as an otolith disease.

The user interface unit 112 receives a webpage (101 in FIG. 3) for providing a self-treatment service from the self-treatment web server 130 and displays it on the screen of the user terminal 110 through an output unit 114.

The control unit 132 of the self-treatment web server 130 compares user information of the inputted ID and password with registered user information and determines whether to permit a login of the user terminal 110 (S102).

When it is determined that the user terminal 110 is permitted to log in, the control unit 132 determines if diagnosis information matched to the user information is stored in the user information database unit 135 (S104).

When diagnosis information is not stored, the control unit 132 provides the user terminal 110 with a self-diagnosis algorithm based on the symptoms described by the patient with BPPV and the disease mechanism of BPPV to allow the user terminal 110 to execute the self-diagnosis algorithm (S106, S108).

The data transmitting unit 134 transmits multiple self-diagnosis questionnaire data to the user terminal 110 in a sequential order.

The user terminal 110 receives the multiple self-diagnosis questionnaire data through the communication unit 113 and executes the self-diagnosis algorithm (S110).

The control unit 132 transmits the self-diagnosis questionnaire data in the form of webpage to the user terminal 110 through the data transmitting unit 134, and the user interface unit 112 outputs the webpage (101 in FIG. 3) provided from the self-treatment web server 130. In this instance, the data input unit 111 of the user terminal 110 displays the self-diagnosis questionnaire data and an input button 115 for "Yes"/"No" choice in response thereto, as shown in FIG. 4.

The control unit 132 receives an answer choice signal to the self-diagnosis questionnaire data from the user terminal 110 and determines the final diagnosis information based on the response to the self-diagnosis questionnaire data (S112).

When the final diagnosis information on the type of BPPV is determined, the control unit 132 retrieves a self-diagnosis and treatment method corresponding to the determined final diagnosis information in the data storage unit 133, and transmits the self-diagnosis and treatment method created in the form of a video to the user terminal 110 through the data transmitting unit 134 (S114).

As shown in FIG. 5, the output unit 114 of the user terminal 110 outputs the final diagnosis information through the self-diagnosis algorithm and its corresponding self-diagnosis and treatment method (canalith repositioning maneuver) in the form of a video (S116).

The control unit 132 transmits self-diagnosis and treatment information including the final diagnosis information and the self-diagnosis and treatment method to a medical faculty through the communication network 120 in the form of a text message or an image, or transmits and stores it in a database (S118).

In the present disclosure, the self-diagnosis questionnaire data includes the first group of questionnaires including one or more questionnaire data for diagnosing BPPV or non-BPPV, the second group of questionnaire including one or more questionnaire data for determining the location of otolith among the vertical and horizontal semicircular canals, the third group of questionnaire including one or more questionnaire data for diagnosing geotropic-HC-BPPV or apogeotropic-HC-BPPV, and the fourth group of questionnaire including one or more questionnaire data for determining the location of otolith between the ears, and particularly, the self-diagnosis questionnaire data include questionnaires that allow the user to make self-diagnosis without other medical devices, and thus it is possible to allow patients with BPPV to diagnose symptoms immediately and accurately without temporal and spatial constraints using a service provided through webpage without a visit to hospitals when the patients have the symptoms, and further, present optimal treatment methods based on the diagnosis results to the patients to receive appropriate treatments.

Herein, it is desirable that the self-diagnosis questionnaire data include a minimum number of item data of questions in consideration of the patients who are not in a condition to answer a complex question due to acute dizziness. In more detail, the first group of questionnaires may include the first questionnaire data, the second questionnaire data and the third questionnaire data, the second group of questionnaires may include the fourth questionnaire data, the third group of questionnaires may include the fifth questionnaire data, and the fourth group of questionnaires may include the sixth questionnaire data, and in this instance, the first questionnaire data may be a questionnaire about feeling dizzy as if he/she or the surroundings are spinning, the second questionnaire data may be a questionnaire about feeling dizzy upon head movements from sitting or lying still position, the third questionnaire data may be a questionnaire about whether the dizziness caused by head movements lasts for three minutes or more or for less than three minutes, the fourth questionnaire data may be a questionnaire about when lying down or getting up, or when turning the head to the left or right side while lying down, which of the two cases is a posture that usually evokes more severe dizziness, the fifth questionnaire data may be a questionnaire about whether spinning dizziness upon turning the head to the left side or right side while lying down lasts for less than one minute or for one minute or more, and the sixth questionnaire data may be a questionnaire about when lying down with the head on the right side and when lying down with the head on the left side, on which side dizziness is more severe.

Accordingly, as illustrated in FIG. 6, the self-diagnosis questionnaire data 200 may consist of six items data. Accordingly, the user terminal 110 outputs the six items data.

As shown in FIG. 6, the self-diagnosis questionnaire data 200 include the first questionnaire data 201, second questionnaire data 202, third questionnaire data 203, fourth questionnaire data 204, fifth questionnaire data 205 and sixth questionnaire data 206.

The first questionnaire data 201 is a questionnaire of "Did you feel dizzy as if you or your surroundings are spinning?", the second questionnaire data 202 is a questionnaire of "Do you feel dizzy upon head movements from sitting or lying still position?", the third questionnaire data 203 is a questionnaire of "How long does the dizziness caused by head movements last? Does it last for three minutes or more, or for less than three minutes?", the fourth questionnaire data 204 is a questionnaire of "When lying down or getting up, and when turning the head to the left or right side while lying down, which of the two cases is a posture that usually evokes more severe dizziness?", the fifth questionnaire data 205 is a questionnaire of "Does spinning dizziness upon turning the head to the left or right side while lying down disappear within one minute? Or does it last for one minute or more?", and the sixth questionnaire data 206 is a questionnaire of "When lying down with the head on the right side and when lying down with the head on the left side, on which side is the dizziness more severe?"

As shown in FIG. 4, the user terminal 110 displays the six questionnaires datum in a sequential order, and input buttons for "Yes"/"No" choice to each questionnaire data.

When diagnosis information is not stored, the control unit 132 executes the self-diagnosis algorithm based on the symptoms described by the patients with BPPV and the disease mechanism of BPPV on the user terminal 110, and a process of executing the self-diagnosis algorithm is described in detail with reference to FIG. 7 as below.

Figure 7:
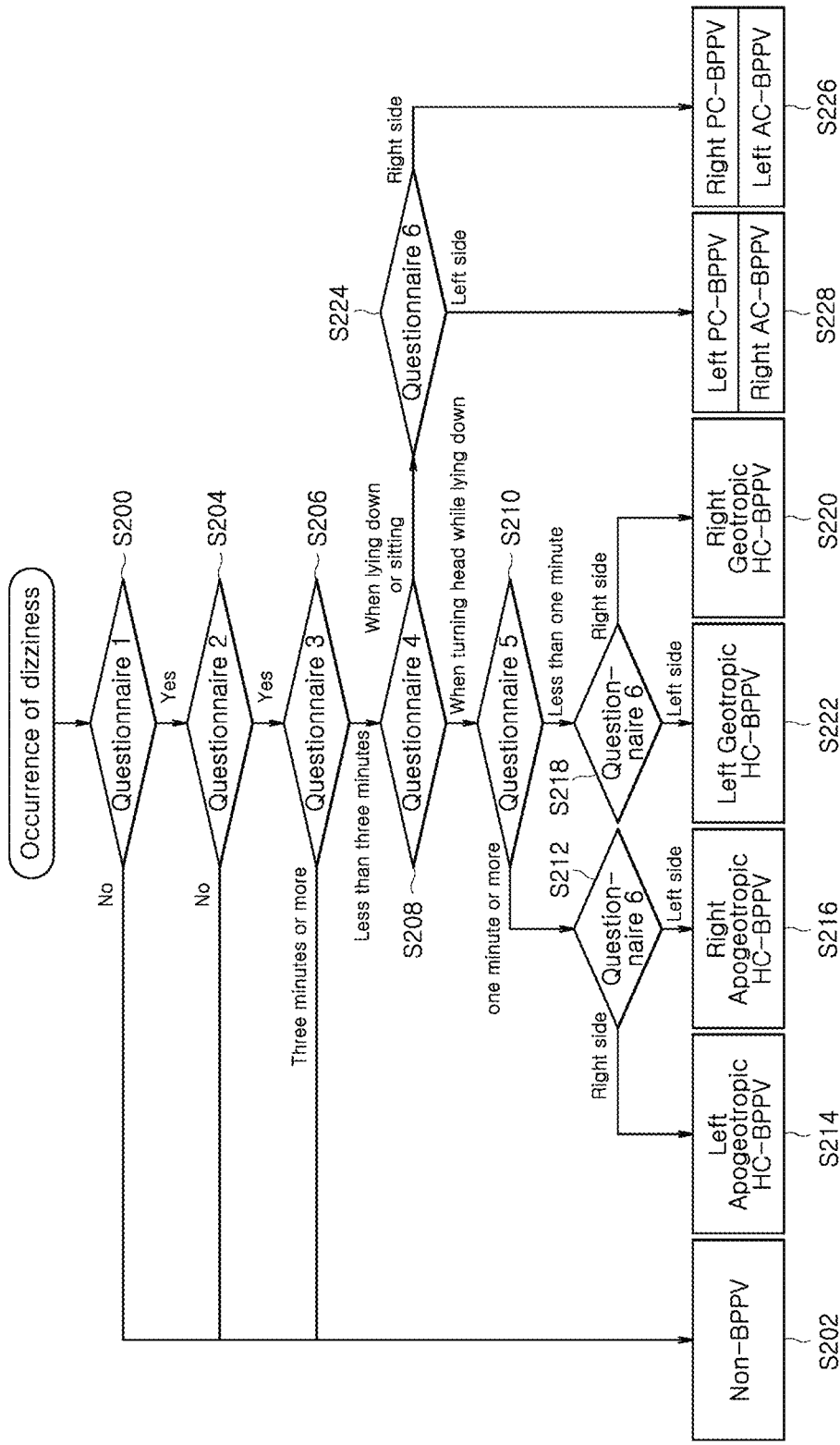
FIG. 7 is a diagram showing a process of executing a self-diagnosis algorithm by a self-treatment web server according to an example of the present disclosure.

FIG. 7 is a diagram showing the process of executing the self-diagnosis algorithm by the self-treatment web server according to an example of the present disclosure, and FIG. 8 is a diagram showing self-diagnosis and treatment methods selected for each type of BPPV according to an example of the present disclosure.

When diagnosis information is not stored, the control unit 132 provides a self-diagnosis algorithm to the user terminal 110.

That is, the control unit 132 transmits the first questionnaire data 201 (e.g., a first question) to the user terminal 110 through the data transmitting unit 134 (S200).

The user terminal 110 receives the first questionnaire data 201 from the self-treatment web server 130 and outputs it to the screen.

The first questionnaire data 201 is a questionnaire of "Did you feel dizzy as if you or your surroundings are spinning?" to determine BPPV or non-BPPV.

BPPV is characterized by spinning dizziness. The spinning dizziness is caused by displacement of otolithic debris into the semicircular canals, which induces endolymph flow when the position of the head is changed, by floating in the canal or attachment to the cupula.

The commonly used phrases when patients describe their symptoms are spinning or ceilings are moving or the like.

When an answer choice signal of "No" is received from the user terminal 110 in the first questionnaire data 201, the control unit 132 classifies as non-BPPV, and generates a self-diagnosis end signal and transmits it to the user terminal 110 (S202). That is, the user terminal 110 does not output the next questionnaire data, and questionnaire ends.

When an answer choice signal of "Yes" is received by the data receiving unit 131 from the user terminal 110 in the first questionnaire data 201, the control unit 132 transmits the second questionnaire data 202 (e.g., a second question) to the user terminal 110 through the data transmitting unit 134 (S204).

The user terminal 110 receives the second questionnaire data 202 from the self-treatment web server 130 and outputs it to the screen.

The second questionnaire data 202 is a questionnaire of "Do you feel dizzy upon head movements from sitting still or lying position?" to determine BPPV or non-BPPV.

The semicircular canals sense rotational head movements. Three semicircular canals are located at the inner sides of two ears and sense head acceleration in a 3-dimensional space.

The semicircular canals are filled with the lymph fluid, and sensory cells reside in the semicircular canals to detect the flow of the lymph fluid and sense the head motion.

When otolithic debris migrates into the semicircular canals and interrupts the flow of lymph, severe spinning dizziness occurs, but otolithic debris only moves when the head changes its positions with respect to gravity, so when being in a still position without changes in the head position, the flow of lymph does not occur.

For this reason, patients with BPPV feel severely dizzy when moving the head or body, but when being in a still position without changing the head position, they do not feel dizzy.

When an answer choice signal of "No" is received from the user terminal 110 in the second questionnaire data 202, the control unit 132 classifies as non-BPPV, and generates a self-diagnosis end signal and transmits it to the user terminal 110 (S202).

When an answer choice signal of "Yes" is received by the data receiving unit 131 from the user terminal 110 in the second questionnaire data 202, the control unit 132 transmits third questionnaire data 203 (e.g., a third question) to the user terminal 110 through the data transmitting unit 134 (S206).

The user terminal 110 receives the third questionnaire data 203 from the self-treatment web server 130 and outputs it to the screen.

The third questionnaire data 203 is a questionnaire of "How long does the dizziness caused by head movements last? Does it last for three minutes or more or for less than three minutes?" to determine BPPV or non-BPPV.

As described above, BPPV causes sudden dizziness upon changes in the position of the head, and the symptoms resolve soon. Dizziness occurring on changing head position mostly disappears within about one minute. This span of time is the time taken until migration of otolithic debris induced by the head movements instantaneously causes the lymph fluid in the semicircular canals to flow and this flow ends.

In most of BPPV where otolithic debris floats in the semicircular canals, dizziness disappears in less than one minute, but when otolithic debris is attached to the cupula of the semicircular canals or located near the cupula, the duration of dizziness may be longer than one minute. For this reason, in the third questionnaire data, a criterion for the duration of dizziness is three minutes.

When dizziness lasts for three minutes or more, it is atypical for BPPV, and when dizziness lasts for less than three minutes, it is determined as BPPV.

When an answer choice signal of "three minutes or more" is received by the data receiving unit 131 from the user terminal 110 in the third questionnaire data 203, the control unit 132 classifies as non-BPPV, and generates a self-diagnosis end signal and transmits it to the user terminal 110 (S202).

When an answer choice signal of "less than three minutes" is received by the data receiving unit 131 from the user terminal 110 in the third questionnaire data 203, the control unit 132 transmits the fourth questionnaire data 204 (e.g., a fourth question) to the user terminal 110 through the data transmitting unit 134 (S208).

The user terminal 110 receives the fourth questionnaire data 204 from the self-treatment web server 130 and outputs it to the screen.

The fourth questionnaire data 204 is a questionnaire of "When lying down or getting up, and when turning the head to the left or right side while lying down, which is the posture that usually evokes more severe dizziness?" to determine the type of BPPV.

Otolithic debris may enter at least one of three semicircular canals, which include the anterior, horizontal (also referred to as lateral), and posterior semicircular canals.

Among the three semicircular canals, the anterior and posterior semicircular canals usually sense vertical movements, and the horizontal semicircular canal senses horizontal movements. Accordingly, it is possible to determine the semicircular canal where otolith entered, by identifying which movement causes otolith disease symptoms, among the vertical movements such as lying down or getting up, and horizontal movements such as turning the head while lying down.

This questionnaire may result in a consistent conclusion in the analysis of symptoms actually described by the patients with BPPV.

When an answer choice signal of "when lying down or getting up" is received by the data receiving unit 131 from the user terminal 110 in the fourth questionnaire data 204, the control unit 132 classifies the disease type as the vertical semicircular canal (anterior or posterior semicircular canal), and when an answer choice signal of "when turning the head to the left or right side while lying down" is received, the control unit 132 classifies the disease type as the horizontal semicircular canal.

When an answer choice signal of "when turning the head to the left or right side while lying down" is received by the data receiving unit 131 from the user terminal 110 in the fourth questionnaire data 204, the control unit 132 transmits the fifth questionnaire data 205 (e.g., a fifth question) to the user terminal 110 through the data transmitting unit 134 (S210).

The user terminal 110 receives the fifth questionnaire data 205 from the self-treatment web server 130 and outputs it to the screen.

The fifth questionnaire data 205 is a questionnaire of "Does the spinning dizziness upon turning the head to the left or right side while lying down disappear within one minute? Or does it last for one minute or more?" to determine whether the otolithic debris is floating in the horizontal semicircular canal (Canalithiasis), or otolithic debris is attached to or located near the cupula (Cupulolithiasis).

Only when an answer choice signal of "when turning the head to the left or right side while lying down" is received by the data receiving unit 131 in the fourth questionnaire data 204 and the disease type is classified as the horizontal semicircular canal, the control unit 132 transmits the fifth questionnaire data 205 to the user terminal 110 (S210).

It is known that apogeotropic HC-BPPV is caused by otolithic debris attached to or located near the cupula of the horizontal semicircular canal, and the duration of dizziness is longer than that of geotropic HC-BPPV that is caused by otolithic debris floating in the horizontal semicircular canal.

Indeed nystagmus of a larger duration is observed in patients with apogeotropic HC-BPPV during examination.

Accordingly, patients having dizziness symptoms that last for one minute or more are classified as apogeotropic HC-BPPV, and patients in which symptoms disappear within one minute are classified as geotropic HC-BPPV.

When an answer choice signal of "one minute or more" is received by the data receiving unit 131 from the user terminal 110 in the fifth questionnaire data 205, the control unit 132 transmits the sixth questionnaire data 206 (e.g., a sixth question) to the user terminal 110 through the data transmitting unit 134 (S212).

The user terminal 110 receives the sixth questionnaire data 206 from the self-treatment web server 130 and outputs it to the screen.

The sixth questionnaire data 206 is a questionnaire of "When lying down with the head on the right side and when lying down with the head on the left side, on which side is dizziness more severe?" to determine which ear is involved.

In patients with PC-BPPV and geotropic HC-BPPV, the sensory cells located in the semicircular canals sense an excitatory signal when the head is turned toward the side of the lesion, and an inhibitory signal when the head is turned toward the side opposite to the lesion. Humans have physiological characteristics that they feel excitatory responses much more severe than inhibitory responses.

For this reason, patients with PC-BPPV and geotropic HC-BPPV have more dizziness when the head is turned toward the side of the lesion, and when the head is turned toward the side opposite to the lesion, they have milder symptoms.

In contrast, in patients with AC-BPPV and apogeotropic the sensory cells located in the semicircular canals sense an excitatory signal when the head is turned away from the lesion side, and an inhibitory signal when the head is turned toward the lesion side.

Accordingly, patients with AC-BPPV and apogeotropic HC-BPPV have more severe dizziness when the head is turned away from the lesion side, and when the head is turned toward the lesion side, they have milder symptoms.

The user terminal 110 displays input buttons of "right side" and "left side".

When an answer choice signal of "right side" is received by the data receiving unit 131 from the user terminal 110 in the sixth questionnaire data 206, the control unit 132 determines the final diagnosis information as left apogeotropic HC-BPPV, and transmits the determined final diagnosis information to the user terminal 110 (S214). Here, HC refers to Horizontal Semicircular Canal.

When an answer choice signal of "left side" is received by the data receiving unit 131 from the user terminal 110 in the sixth questionnaire data 206, the control unit 132 determines the final diagnosis information as Right Apogeotropic HC-BPPV, and transmits the determined final diagnosis information to the user terminal 110 (S216).

When an answer choice signal of "less than one minute" is received by the data receiving unit 131 from the user terminal 110 in the fifth questionnaire data 205, the control unit 132 transmits the sixth questionnaire data 206 to the user terminal 110 through the data transmitting unit 134 (S218).

The user terminal 110 receives the sixth questionnaire data 206 from the self-treatment web server 130 and outputs it to the screen.

When an answer choice signal of "right side" is received by the data receiving unit 131 from the user terminal 110 in the sixth questionnaire data 206, the control unit 132 determines the final diagnosis information to be Right Geotropic-HC-BPPV, and transmits the determined final diagnosis information to the user terminal 110 (S220).

When an answer choice signal of "left side" is received by the data receiving unit 131 from the user terminal 110 in the sixth questionnaire data 206, the control unit 132 determines the final diagnosis information as Left Geotropic-HC-BPPV, and transmits the determined final diagnosis information to the user terminal 110 (S222).

When an answer choice signal of "when lying down or getting up" is received by the data receiving unit 131 from the user terminal 110 in the fourth questionnaire data 204, the control unit 132 classifies the disease type as the vertical semicircular canal (anterior or posterior semicircular canals) and transmits the sixth questionnaire data 206 to the user terminal 110 (S224).

The user terminal 110 receives the sixth questionnaire data 206 from the control unit 132 and outputs it to the screen.

When an answer choice signal of "right side" is received by the data receiving unit 131 from the user terminal 110 in the sixth questionnaire data 206, the control unit 132 determines the final diagnosis information as Right PC-BPPV or Left AC-BPPV, and transmits the determined final diagnosis information to the user terminal 110 (S226). Here, PC refers to Posterior Semicircular Canal, and AC refers to Anterior Semicircular Canal.

When an answer choice signal of "left side" is received by the data receiving unit 131 from the user terminal 110 in the sixth questionnaire data 206, the control unit 132 determines the final diagnosis information as Left PC-BPPV or Right AC-BPPV, and transmits the determined final diagnosis information to the user terminal 110 (S228).

The control unit 132 may determine whether BPPV occurred or not (BPPV or non-BPPV) based on the first to sixth questionnaire data 206, and when BPPV occurs, may determine the disease type based on the involved canal and the location of otolithic debris in each semicircular canal.

As described above, the type of BPPV is classified into Right PC-BPPV or Left AC-BPPV, Left PC-BPPV or Right AC-BPPV, Right Apogeotropic-HC-BPPV, Left Apogeotropic-HC-BPPV, Right Geotropic-HC-BPPV and Left Geotropic-HC-BPPV.

Among the disease types of BPPV, Right PC-BPPV, Left AC-BPPV, Left PC-BPPV and Right AC-BPPV are different in the involved canal, but their symptoms and treatment methods for Right PC-BPPV and Left AC-BPPV are same, and thus it does not affect self-diagnosis and self-treatment even though they are grouped into the same category, and this is the case as well for Left PC-BPPV and Right AC-BPPV. The present disclose combines these features into the algorithm of its system so as to result in the best on-site self-diagnosis and self-treatment by patients who do not have special medical knowledge as well as medical devices such as video-oculography. For reference, medical devices such as video-oculography are necessary to distinguish PC-BPPV from AC-BPPV.

That is, the system according to the present disclosure does not distinguish PC-BPPV from AC-BPPV, which rather allows the system to provide immediate, easy and efficient on-site self-diagnosis and self-treatment by patients themselves in an optimized way.

The above-described self-diagnosis algorithm depicts a process of deriving the disease type of BPPV based on the first to sixth questionnaire data 206 as shown in FIG. 7.

When the final diagnosis information for the type of BPPV is determined, the control unit 132 searches for a self-diagnosis and treatment method corresponding to the determined final diagnosis information in the data storage unit 133, and transmits the self-diagnosis and treatment method created in the form of a video to the user terminal 110.

The user terminal 110 outputs the final diagnosis information outputted by the self-diagnosis algorithm and its corresponding self-diagnosis and treatment method (canalith repositioning maneuver) in the form of a video.

The treatment method for BPPV uses the canalith repositioning maneuver that includes serial changes in the head position for treatment of BPPV by moving the dislodged otolith back into the original place.

The canalith repositioning maneuver varies depending on the type of BPPV, and a treatment method with the highest treatment success rate is selected from the known treatment methods. The selected treatment method is already known, and its detailed description is omitted herein.

The data storage unit 133 creates and stores the selected self-diagnosis and treatment method 300 in the form of a video file to allow the patient to easily understand and repeat.

As shown in FIG. 8, self-diagnosis and treatment methods (canalith repositioning maneuvers) 300 selected for each disease type of BPPV are as follows.

When the final diagnosis information is Non-BPPV, the control unit 132 provides the user terminal 110 with Brand-Daroff Exercise 301 in the form of a video, when the final diagnosis information is Left Apogeotropic-HC-BPPV, provides the user terminal 110 with Gufoni maneuver for left cupulolithiasis 302 in the form of a video, and when the final diagnosis information is Right Apogeotropic-HC-BPPV, provides the user terminal 110 with Gufoni maneuver for right cupulolithiasis 303 in the form of a video.

When the final diagnosis information is Left Geotropic-HC-BPPV, the control unit 132 provides the user terminal 110 with Barbecue maneuver for left geotropic-HC-BPPV 304 in the form of a video, and when the final diagnosis information is Right Geotropic-HC-BPPV, provides the user terminal 110 with Barbecue maneuver for right geotropic-HC-BPPV 305 in the form of a video.

When the final diagnosis information is Left PC-BPPV or Right AC-BPPV, the control unit 132 provides the user terminal 110 with Epley maneuver for left PC-BPPV 306 in the form of a video, and when the final diagnosis information is Right PC-BPPV or Left AC-BPPV, provides the user terminal 110 with Epley maneuver for right PC-BPPV 307.

Meanwhile, according to an example of the present disclosure, the user terminal 110 may connect to the self-diagnosis web server 130 and the self-diagnosis web server 130 may perform diagnosis of BPPV, but the present disclosure is not necessarily limited thereto, and the user terminal 110 may directly perform diagnosis of BPPV.

In this instance, the user terminal 110 may include a user interface unit 112 to provide a user with multi-step self-diagnosis questionnaire data related to diagnosis of BPPV, a data input unit 111 to receive the input of one or more response data to the self-diagnosis questionnaire data, and a control unit (not shown) to determine a final diagnosis information based on the one or more response data, and herein, the self-diagnosis questionnaire data includes a first group of questionnaires including one or more questionnaire data for diagnosing BPPV or Non-BPPV, a second group of questionnaires including one or more questionnaire data for determining location of otolith among vertical and horizontal semicircular canals, a third group of questionnaires including one or more questionnaire data for diagnosing Geotropic-HC-BPPV or Apogeotropic-HC-BPPV, and a fourth group of questionnaires including one or more questionnaire data for diagnosing a location of otolith between the ears, and the self-diagnosis questionnaire data include questionnaires that allow the user to make self-diagnosis without other medical device, to enable the user terminal 110 to directly perform diagnosis of BPPV independently from the self-treatment web server 130.

Further, the user terminal 110 may further include a data storage unit (not shown) to store a self-treatment method selected for each type of BPPV from the data storage unit 133 provided in the self-treatment web server 130 and created in the form of a video, or may receive the self-treatment method in the form of a video from the data storage unit 133 provided in the self-treatment web server 130, and accordingly, the control unit (not shown) of the user terminal 110 may determine the final diagnosis information based on the one or more response data, search for a self-treatment method corresponding to the determined final diagnosis information in the data storage unit, and provide the searched self-treatment method to the user.

Further, a method for self-diagnosis and/or treatment of BPPV using a device for self-diagnosis of BPPV including a self-treatment web server 130 including a data transmitting unit 134, a data receiving unit 131 and a control unit 132 according to a feature of the present disclosure includes: transmitting, by the control unit 132, multiple self-diagnosis questionnaire data related to treatment of BPPV to the user terminal 110 through the data transmitting unit 134; receiving, by the data receiving unit 131, one or more response data to the self-diagnosis questionnaire data from the user terminal 110; and determining, by the control unit 134, a final diagnosis information based on the one or more response data, and the self-diagnosis questionnaire data include a first group of questionnaires including one or more questionnaire data for diagnosing BPPV or Non-BPPV, a second group of questionnaires including one or more questionnaire data for diagnosing a location of otolith among vertical and horizontal semicircular canals, a third group of questionnaires including one or more questionnaire data for diagnosing Geotropic-HC-BPPV or Apogeotropic-HC-BPPV, and a fourth group of questionnaires including one or more questionnaire data for diagnosing a location of otolith between the ears, and the self-diagnosis algorithm allows a user to make self-diagnosis without other medical device.

Herein, the device for self-diagnosis of BPPV including the self-treatment web server 130 includes one or more processor devices, a memory device and a communication device, and operates through the processor device through a computer program stored in the memory device and performs data communication with the user terminal 110 through a communication module to perform the method for self-diagnosis and/or treatment of BPPV using the device for self-diagnosis and/or treatment of BPPV according to an example of the present disclosure.

Additionally, a method for self-diagnosis and/or treatment of BPPV using a device for self-diagnosis and/or treatment of BPPV including a user terminal 110 including a user interface unit 112, a data input unit 111 and a control unit (not shown) according to a feature of the present disclosure may include: providing, by the user interface unit 111, a user with multi-step self-diagnosis questionnaire data related to diagnosis of BPPV; receiving, by the data input unit 111, the input of one or more response data to the self-diagnosis questionnaire data; and determining, by the control unit (not shown), a final diagnosis information based on the one or more response data, and herein, the self-diagnosis questionnaire data include a first group of questionnaires including one or more questionnaire data for diagnosing BPPV or Non-BPPV, a second group of questionnaires including one or more questionnaire data for diagnosing a location of otolith among vertical and horizontal semicircular canals, a third group of questionnaires including one or more questionnaire data for diagnosing Geotropic-HC-BPPV or Apogeotropic-HC-BPPV, and a fourth group of questionnaires including one or more questionnaire data for diagnosing a location of otolith between the ears, and particularly, the self-diagnosis algorithm allows a user to make self-diagnosis without other medical device.

Herein, the device for self-diagnosis and/or treatment of BPPV including the user terminal 110 includes one or more processor devices, a memory device, a display device, a user input device and a communication device, and operates through the processor device through a computer program stored in the memory device, provides self-diagnosis questionnaire data to the user through the display device, receives the input of one or more response data to the self-diagnosis questionnaire data from the user through the user input device, and determines the final diagnosis information based on the one or more response data via data communication with the self-treatment web server 130 through a communication module or without connection of the user terminal 110 with the self-treatment web server 130, to implement the method for self-diagnosis of BPPV using the device for self-diagnosis and/or treatment of BPPV according to an example of the present disclosure.

Additionally, a computer program according to another aspect of the present disclosure is a computer program stored in a computer-readable medium to enable a computer to perform each step of the method for self-diagnosis and/or treatment of BPPV as described previously. The computer program may be a computer program including machine code generated by a compiler, as well as a computer program including high-level language code that can be executed by a computer using an interpreter, etc. Herein, the computer is not limited to a personal computer (PC) or a laptop computer, etc., and includes any type of information processing device with a central processing unit (CPU) to execute the computer program, for example, a server, a smart phone, a tablet PC, PDA, a mobile phone and the like. Additionally, the computer-readable medium includes any type of computer-readable storage media such as electronic recording media (for example, ROM, flash memory, etc.), magnetic storage media (for example, floppy disk, hard disk, etc.) and optical readable media (for example, CD-ROM, DVD, etc.) and the like.

Accordingly, the device, method and computer program for self-diagnosis and/or treatment of BPPV according to an example of the present disclosure allows the user to make self-diagnosis of BPPV without temporal and spatial constraints using self-diagnosis questionnaire data including the questionnaires allowing for self-diagnosis without other medical device with a sufficiently high accuracy of diagnosis to achieve medical usefulness, and further, presents an optimal treatment method based on the diagnosis results to allow the user to receive appropriate treatment.

In more detail, as a result of diagnosing 578 patients using the device, method and computer program for self-diagnosis and/or treatment of BPPV according to an example of the present disclosure, the effectiveness of the present disclosure is demonstrated as below.

First, as a result of diagnosis according to the device, method and computer program for self-diagnosis of BPPV according to an example of the present disclosure, among 578 patients, 378 patients are classified as Non-BPPV in the first group of questionnaires.

In this instance, as a result of the existing thorough examination of BPPV in the above 378 patients, only 7% of them is diagnosed with BPPV, and it can be seen that it is possible to diagnose BPPV with a high accuracy of 93%.

Further, for 200 patients classified as BPPV in the first group of questionnaires, the disease type of BPPV is diagnosed for each patient through the second, third and fourth group of questionnaires according to the present disclosure, and as a result of comparing with the diagnosis results using the existing video eye movement examination equipment, among the 200 patients, consistency of the diagnosis results of 121 patients is observed (60.5%) and the degree of consistency is found statistically very high (Cohen's Kappa index=0.673), so it can be seen that the device, method and computer program for self-diagnosis and/or treatment of BPPV according to an example of the present disclosure can achieve self-diagnosis and/or treatment of BPPV with a very high accuracy without other medical device As described above, in contrast to the related art, in the present disclosure, the self-diagnosis algorithm associated with the self-diagnosis questionnaire data is provided for sequentially screening BPPV versus Non-BPPV first and followed by determining the subtype and affected ear of BPPV in best efficient and optimized way using optimized self-diagnosis questionnaire data.

This sequential and efficient self-diagnosis algorithm associated with the optimized self-diagnosis questionnaire data and the system of the present disclosure may allow all patients who appeal and present with dizziness to easily and conveniently diagnose and treat BPPV by patients themselves on-site, for example at home, even though they do not have any special medical knowledge related to dizziness or BPPV, and also allow a platform providing a whole process of diagnose and treatment of BPPV without temporal or spatial constraints.

While the examples of the present disclosure have been hereinabove described in detail, the scope of the present disclosure is not limited thereto, and many changes and modifications made by those skilled in the art using the basic concept of the present disclosure defined in the appended claims also fall in the scope of the present disclosure.

What is claimed is:

1. A device comprising:
   at least one processor; and
   memory storing instructions that, when executed by the at least one processor, cause the device to:
   transmit, to a user terminal and via a communication network, multi-step self-diagnosis questionnaire data related to diagnosis of benign paroxysmal positional vertigo (BPPV);
   receive, from the user terminal, response data to the multi-step self-diagnosis questionnaire data; and
   determine, based on the response data and a self-diagnosis algorithm associated with the multi-step self-diagnosis questionnaire data, diagnosis information,
   wherein the multi-step self-diagnosis questionnaire data comprises:
   a first question relating to whether a user feels dizzy as if the user or surroundings of the user are spinning,
   a second question relating to whether the user feels dizzy upon making a head movement after sitting still or rising from a lying position,
   a third question relating to whether dizziness caused by the head movement lasts for more than three minutes,
   a fourth question relating to whether lying down or getting up by the user causes more severe dizziness than a lateral head movement by the user while lying down,
   a fifth question relating to whether dizziness caused by the lateral head movement of the user while lying down lasts for less than one minute, and
   a sixth question relating to whether the dizziness is more severe when the user is lying down on a right side of the head or on a left side of the head,
   wherein the self-diagnosis algorithm comprises:
   a first diagnosis of determining one of BPPV or Non-BPPV based on answers to the first question, the second question, and the third question; and
   a second diagnosis of determining, based on a result of the first diagnosis and an answer to the fourth question, that a location of an otolithic debris is in a vertical semicircular canal or a horizontal semicircular canal;
   a third diagnosis of determining, based on a result of the second diagnosis and an answer to the fifth question, one of geotropic horizontal-canal BPPV (Geotropic-HC-BPPV) or apogeotropic horizontal-canal BPPV (Apogeotropic-HC-BPPV); and
   a fourth diagnosis of determining, based on at least one of the result of the second diagnosis or a result of the third diagnosis, and an answer to the sixth question, that the location of the otolithic debris is in a right ear or a left ear.

2. The device of claim 1, wherein the diagnosis information indicates Left Apogeotropic-HC-BPPV in response to the response data comprising:
   an affirmative response signal responsive to the first question,
   an affirmative response signal responsive to the second question,
   a response signal, responsive to the third question, indicating the dizziness caused by the head movement lasts for less than three minutes,
   a response signal, responsive to the fourth question, indicating that the lateral head movement by the user while lying down causes the more severe dizziness,
   a response signal, responsive to the fifth question, indicating that the dizziness caused by the lateral head movement of the user while lying down lasts for more than one minute, and
   a response signal, responsive to the sixth question, indicating that the dizziness is more severe when the user is lying down on the right side of the head,
   wherein the diagnosis information indicates Right Apogeotropic-HC-BPPV in response to the response data comprising:
   the affirmative response signal responsive to the first question,
   the affirmative response signal responsive to the second question,
   the response signal, responsive to the third question, indicating the dizziness caused by the head movement lasts for less than three minutes,
   the response signal, responsive to the fourth question, indicating that the lateral head movement by the user while lying down causes the more severe dizziness,
   p2 the response signal, responsive to the fifth question, indicating that the dizziness caused by the lateral head movement of the user while lying down lasts for more than one minute, and
   a response signal, responsive to the sixth question, indicating that the dizziness is more severe when the user is lying down on the left side of the head,
   wherein the diagnosis information indicates Right Geotropic-HC-BPPV in response to the response data comprising:
   the affirmative response signal responsive to the first question,
   the affirmative response signal responsive to the second question,
   the response signal, responsive to the third question, indicating the dizziness caused by the head movement lasts for less than three minutes,
   the response signal, responsive to the fourth question, indicating that the lateral head movement by the user while lying down causes the more severe dizziness,
   a response signal, responsive to the fifth question, indicating that the dizziness caused by the lateral head movement of the user while lying down lasts for less than one minute, and
   the response signal, responsive to the sixth question, indicating that the dizziness is more severe when the user is lying down on the right side of the head, and
   wherein the diagnosis information indicates Left Geotropic-HC-BPPV in response to the response data comprising:
   the affirmative response signal responsive to the first question,
   the affirmative response signal responsive to the second question,
   the response signal, responsive to the third question, indicating the dizziness caused by the head movement lasts for less than three minutes, the response signal, responsive to the fourth question, indicating that the lateral head movement by the user while lying down causes the more severe dizziness, the response signal, responsive to the fifth question, indicating that the dizziness caused by the lateral head movement of the user while lying down lasts for less than one minute, and a response signal, responsive to the sixth question, indicating that the dizziness is more severe when the user is lying down on the left side of the head.

3. The device of claim 1, wherein the diagnosis information indicates one of Right posterior-canal BPPV (PC-BPPV) or Left anterior-canal BPPV (AC-BPPV) in response to the response data comprising:

an affirmative response signal responsive to the first question, an affirmative response signal responsive to the second question, a response signal, responsive to the third question, indicating the dizziness caused by the head movement lasts for less than three minutes, a response signal, responsive to the fourth question, indicating that lying down or getting up by the user causes the more severe dizziness, and a response signal, responsive to the sixth question, indicating that the dizziness is more severe when the user is lying down on the right side of the head, and wherein the diagnosis information indicates one of Left PC-BPPV or Right AC-BPPV in response to the response data comprising:

the affirmative response signal responsive to the first question, the affirmative response signal responsive to the second question, the response signal, responsive to the third question, indicating the dizziness caused by the head movement lasts for less than three minutes, the response signal, responsive to the fourth question, indicating that lying down or getting up by the user causes the more severe dizziness, and a response signal, responsive to the sixth question, indicating that the dizziness is more severe when the user is lying down on the left side of the head.

4. The device of claim 1, wherein the instructions, when executed by the at least one processor, further cause the device to:

store, in data storage, a video about a self-administered treatment selected for each disease type of BPPV, and search, in the data storage, for the video about the self-administered treatment corresponding to the determined diagnosis information, and transmit the video to the user terminal.

5. The device of claim 1, wherein the instructions, when executed by the at least one processor, further cause the device to:

in response to the diagnosis information indicating Left Apogeotropic-HC-BPPV, transmitting, to the user terminal, a video related to Gufoni maneuver for left cupulolithiasis, and in response to the diagnosis information indicating Right Apogeotropic-HC-BPPV, transmitting, to the user terminal, a video related to Gufoni maneuver for right cupulolithiasis.

6. The device of claim 1, wherein the instructions, when executed by the at least one processor, further cause the device to:

in response to the diagnosis information indicating Left Geotropic-HC-BPPV, transmitting, to the user terminal, a video related to Barbecue maneuver for left geotropic-HC-BPPV, and in response to the diagnosis information indicating Right Geotropic-HC- BPPV, transmitting, to the user terminal, a video related to Barbecue maneuver for right geotropic-HC-BPPV.

7. The device of claim 1, wherein the instructions, when executed by the at least one processor, further cause the device to:

in response to the diagnosis information indicating Left PC-BPPV or Right AC-BPPV, transmitting, to the user terminal, a video related to Epley maneuver for left PC-BPPV, and in response to the diagnosis information indicating Right PC-BPPV or Left AC-BPPV, transmitting, to the user terminal, a video related to Epley maneuver for right PC-BPPV.

8. A device comprising:

at least one processor;

a user interface; and memory storing instructions that, when executed by the at least one processor, cause the device to:

present, to a user via the user interface, multi-step self-diagnosis questionnaire data related to diagnosis of benign paroxysmal positional vertigo (BPPV);

receive an input of response data to the multi-step self-diagnosis questionnaire data; and determine based on the response data and a self-diagnosis algorithm associated with the multi-step self-diagnosis questionnaire data, diagnosis information, wherein the multi-step self-diagnosis questionnaire data comprises:

a first question relating to whether a user feels dizzy as if the user or surroundings of the user are spinning, a second question relating to whether the user feels dizzy upon making a head movement after sitting still or rising from a lying position, a third question relating to whether dizziness caused by the head movement lasts for more than three minutes, a fourth question relating to whether lying down or getting up by the user causes more severe dizziness than a lateral head movement by the user while lying down, a fifth question relating to whether dizziness caused by the lateral head movement of the user while lying down lasts for less than one minute, and a sixth question relating to whether the dizziness is more severe when the user is lying down on a right side of the head or on a left side of the head, wherein the self-diagnosis comprises:

a first diagnosis of determining one of BPPV or Non-BPPV based on answers to the first question, the second question, and the third question;

a second diagnosis, of determining, based on a result of the first diagnosis and an answer to the fourth question, that a location of an otolithic debris is in a vertical semicircular canal or a horizontal semicircular canal;

a third diagnosis of determining, based on a result of the second diagnosis and an answer to the fifth question, one of geotropic horizontal-Canal BPPV (Geotropic-HC-BPPV) or apogeotropic horizontal-canal BPPV (Apogeotropic-HC-BPPV); and a fourth diagnosis of determining, based on at least one of the result of the second diagnosis or a result of the third diagnosis, and an answer to the sixth question, that the location of the otolithic debris is in a right ear or a left ear.

9. A method comprising:
transmitting, by a device and to a user terminal, multi-step self-diagnosis questionnaire data related to diagnosis of benign paroxysmal positional vertigo (BPPV);
receiving, from the user terminal, response data to the multi-step self- diagnosis questionnaire data; and
determining, by the device and based on the response data and a self-diagnosis algorithm associated with the multi-step self-diagnosis questionnaire data, diagnosis information,
wherein the multi-step self-diagnosis questionnaire data comprises:
a first question relating to whether a user feels dizzy as if the user or surroundings of the user are spinning,
a second question relating to whether the user feels dizzy upon making a head movement after sitting still or rising from a lying position,
a third question relating to whether dizziness caused by the head movement lasts for more than three minutes,
a fourth question relating to whether lying down or getting up by the user causes more severe dizziness than a lateral head movement by the user while lying down,
a fifth question relating to whether dizziness caused by the lateral head movement of the user while lying down lasts for less than one minute, and
a sixth question relating to whether the dizziness is more severe when the user is lying down on a right side of the head or on a left side of the head,
wherein the self-diagnosis algorithm comprises:
a first diagnosis of determining one of BPPV or Non-BPPV based on answers to the first question, the second question, and the third question;
a second diagnosis of determining, based on a result of the first diagnosis and an answer to the fourth question, that a location of an otolithic debris is in a vertical semicircular canal or a horizontal semicircular canal;
a third diagnosis of determining, based on a result of the second diagnosis and an answer to the fifth question, one of geotropic horizontal-canal BPPV (Geotropic-HC-BPPV or apogeotropic horizontal-canal BPPV (Apogeotropic-HC-BPPV); and
a fourth diagnosis of determining, based on at least one of the result of the second diagnosis or a result of the third diagnosis, and an answer to the sixth question, that the location of the otolithic debris.

10. The method of claim 9, wherein the first question, the second question, and the third question are transmitted to the user terminal in a sequential order, and
wherein the diagnosis information indicates Non-BPPV in response to the response data comprising:
a negative response signal responsive to the first question,
a negative response signal responsive to the second question, and
a response signal, response to the third question, indicating the dizziness caused by the head movement lasts for more than three minutes.

11. The method of claim 9, wherein the first question, the second question, and the third question are transmitted to the user terminal in a sequential order,
wherein the diagnosis information indicates BPPV in response to the response data comprising:
an affirmative response signal responsive to the first question,
an affirmative response signal responsive to the second question, and
a response signal, response to the third question, indicating the dizziness caused by the head movement lasts for less than three minutes, and
wherein the diagnosis information indicates a horizontal semicircular canal and the fifth question is transmitted to the user terminal, in response to the response data comprising a response signal, responsive to the fourth question, indicating that the lateral head movement by the user while lying down causes the more severe dizziness.

12. The method of claim 11, wherein the diagnosis information indicates Apogeotrpic-HC-BPPV and the sixth question is transmitted to the user terminal, in response to the response data comprising a response signal, responsive to the fifth question, indicating that the dizziness caused by the lateral head movement of the user while lying down lasts for more than one minute,
wherein the diagnosis information indicates Left Apogeotropic-HC-BPPV in response to the response data comprising:
the response signal, responsive to the fifth question, indicating that the dizziness caused by the lateral head movement of the user while lying down lasts for more than one minute, and
a response signal, responsive to the sixth question, indicating that the dizziness is more severe when the user is lying down on the right side of the head,
wherein the diagnosis information indicates Right Apogeotrpic-HC-BPPV in response to the response data comprising:
the response signal, responsive to the fifth question, indicating that the dizziness caused by the lateral head movement of the user while lying down lasts for more than one minute, and
a response signal, responsive to the sixth question, indicating that the dizziness is more severe when the user is lying down on the left side of the head,
wherein the diagnosis information indicates Geotropic-HC-BPPV and the sixth question is transmitted to the user terminal, in response to the response data comprising a response signal, responsive to the fifth question, indicating that the dizziness caused by the lateral head movement of the user while lying down lasts for less than one minute,
wherein the diagnosis information indicates Right Geotropic-HC-BPPV in response to the response data comprising:
the response signal, responsive to the fifth question, indicating that the dizziness caused by the lateral head movement of the user while lying down lasts for less than one minute, and
the response signal, responsive to the sixth question, indicating that the dizziness is more severe when the user is lying down on the right side of the head, and
wherein the diagnosis information indicates Left Geotropic-HC-BPPV in response to the response data comprising:

the response signal, responsive to the fifth question, indicating that the dizziness caused by the lateral head movement of the user while lying down lasts for less than one minute, and the response signal, responsive to the sixth question, indicating that the dizziness is more severe when the user is lying down on the left side of the head.

13. The method of claim 9, wherein the first question, the second question, and the third question are transmitted to the user terminal in a sequential order, and wherein the diagnosis information indicates BPPV in response to the response data comprising:
an affirmative response signal responsive to the first question,
an affirmative response signal responsive to the second question, and
a response signal, responsive to the third question, indicating the dizziness caused by the head movement lasts for less than three minutes, wherein the diagnosis information indicates a vertical semicircular canal and the sixth question is transmitted to the user terminal, in response to the response data comprising a response signal, responsive to the fourth question, indicating that lying down or getting up by the user causes the more severe dizziness, wherein the vertical semicircular canal is one of an anterior semicircular canal or a posterior semicircular canal, wherein the diagnosis information indicates one of Right PC-BPPV or Left AC-BPPV in response to the response data comprising a response signal, responsive to the sixth question, indicating that the dizziness is more severe when the user is lying down on the right side of the head, and wherein the diagnosis information indicates one of Left PC-BPPV or Right AC-BPPV in response to the response data comprising a response signal, responsive to the sixth question, indicating that the dizziness is more severe when the user is lying down on the left side of the head.

14. The method of claim 9, further comprising:
Storing, in data storage, a video about a self-administered treatment selected for each disease type of BPPV, and
searching, in the data storage, for the video about the self-administered treatment corresponding to the determined diagnosis information, and
transmitting the video to the user terminal.

15. A method:
presenting, to a user via a user interface of a device, multi-step self-diagnosis questionnaire data related to diagnosis of benign paroxysmal positional vertigo (BPPV);
receiving an input of response data to the multi-step self-diagnosis questionnaire data; and
determining, based on the response data and a self-diagnosis algorithm associated with the multi-step self-diagnosis questionnaire data, diagnosis information,
wherein the multi-step self-diagnosis questionnaire data comprises:
a first question relating to whether the user feels dizzy as if the user or surroundings of the user are spinning,
a second question relating to whether the user feels dizzy upon making a head movement after sitting still or rising from a lying position,
a third question relating to whether dizziness caused by the head movement lasts for more than three minutes,
a fourth question relating to whether lying down or getting up by the user causes more severe dizziness than a lateral head movement by the user while lying down,
a fifth question relating to whether dizziness caused by the lateral head movement of the user while lying down lasts for less than one minute, and
a sixth question relating to whether the dizziness is more severe when the user is lying down on a right side of the head or on a left side of the head,
wherein the self-diagnosis comprises:
a first diagnosis of determining one of BPPV or Non-BPPV based on answers to the first question, the second question, and the third question;
a second diagnosis, of determining, based on a result of the first diagnosis and an answer to the fourth question, that a location of an otolithic debris is in a vertical semicircular canal or a horizontal semicircular canal;
a third diagnosis of determining, based on a result of the second diagnosis and an answer to the fifth question, one of geotropic horizontal-Canal BPPV (Geotropic-HC-BPPV) or apogeotropic horizontal-canal BPPV (Apogeotropic-HC-BPPV); and
a fourth diagnosis of determining, based on at least one of the result of the second diagnosis or a result of the third diagnosis, and from an answer to the sixth question, that the location of the otolithic debris is a right ear or a left ear.

16. A non-transitory computer-readable medium storing instructions that, when executed by a device, cause the device to:
transmit, to a user terminal, self-diagnosis questionnaire data related to diagnosis of benign paroxysmal positional vertigo (BPPV);
receive, from the user terminal, response data to the self-diagnosis questionnaire data; and
determine, based on the response data and a self-diagnosis algorithm associated with the self-diagnosis questionnaire data, diagnosis information,
wherein the self-diagnosis questionnaire data comprises:
a first question relating to whether the user feels dizzy as if the user or surroundings of the user are spinning,
a second question relating to whether the user feels dizzy upon making a head movement after sitting still or rising from a lying position,
a third question relating to whether dizziness caused by the head movement lasts for more than three minutes,
a fourth question relating to whether lying down or getting up by the user causes more severe dizziness than a lateral head movement by the user while lying down,
a fifth question relating to whether dizziness caused by the lateral head movement of the user while lying down lasts for less than one minute, and
a sixth question relating to whether the dizziness is more severe when the user is lying down on a right side of the head or on a left side of the head,
wherein the self-diagnosis algorithm comprises:
a first diagnosis of determining one of BPPV or Non-BPPV based on answers to the first question, second question, and the third question;
a second diagnosis of determining, based on a result of the first diagnosis and an answer to the fourth question, that a location of an otolithic debris is in a vertical semicircular canal or a horizontal semicircular canal;

a third diagnosis of determining, based on a result of the second diagnosis and an answer to the fifth question, one of geotropic horizontal-canal BPPV (Geotropic-HC-BPPV or apogeotropic horizontal-canal BPPV (Apogeotropic-HC-BPPV); and a fourth diagnosis of determining, based on at least one of the result of the second diagnosis or a result of the third diagnosis, and an answer to the sixth question, that the location of the otolithic debris is in a right ear or a left ear.

\* \* \* \* \*